United States Patent [19]

Manchand et al.

[11] Patent Number: 6,008,209
[45] Date of Patent: Dec. 28, 1999

[54] METHOD OF USING VITAMIN $D_3$ ANALOGS WITH BIS C-20 SIDE CHAINS

[75] Inventors: Percy Sarwood Manchand, Montclair; Milan Radoje Uskokovic, Upper Montclair, both of N.J.

[73] Assignees: Hoffmann-La Roche Inc., Nutley, N.J.; Syntex (U.S.A.), Palo Alto, Calif.

[21] Appl. No.: 09/061,535

[22] Filed: Apr. 16, 1998

Related U.S. Application Data

[60] Provisional application No. 60/044,981, Apr. 28, 1997, and provisional application No. 60/072,182, Jan. 22, 1998.

[51] Int. Cl.[6] .................... A61K 31/595; A61K 31/035; A61K 31/045

[52] U.S. Cl. .................... 514/168; 514/167; 514/738; 514/739; 514/743; 514/744; 514/745; 514/746; 514/747; 514/759

[58] Field of Search ............... 514/167, 168, 514/738, 739, 743, 744, 745, 746, 747, 759

[56] References Cited

U.S. PATENT DOCUMENTS

| | | | |
|---|---|---|---|
| 5,086,191 | 2/1992 | DeLuca et al. | 552/653 |
| 5,087,619 | 2/1992 | Baggiolini et al. | 514/167 |
| 5,384,314 | 1/1995 | Doran et al. | 514/167 |
| 5,428,029 | 6/1995 | Doran et al. | 514/167 |
| 5,451,574 | 9/1995 | Baggiolini et al. | 514/167 |
| 5,696,103 | 12/1997 | Nestor et al. | 514/167 |
| 5,872,120 | 2/1999 | Nakai et al. | 514/254 |
| 5,891,866 | 4/1999 | Doré et al. | 514/168 |

FOREIGN PATENT DOCUMENTS

| | | |
|---|---|---|
| 808 832 | 11/1997 | European Pat. Off. . |
| WO 96/31216 | 10/1996 | WIPO . |

OTHER PUBLICATIONS

Aerssens, et al. Calcif. Tissue Int. 55:pp. 443–450 (1994).
Dechant and Goa, "Calcitrol," New Zealand Drugs and Aging 5(4): pp. 300–317 (1994).
Shiuey, et al. J. Org. Chem. 55: pp. 243–247 (1990).
Kiegel, J. et al., Tetr. Lett. 32: pp. 6057–6060 (1991).
Perlman, K.L. et al., Tetr. Lett. 32: pp. 7663–7666 (1991).
Wovkulich, P.M. et al. Tetrahedron, 40: p. 2283 (1984).
T. Suda, et al. Biochemistry vol. 9, No. 14, 1970 pp. 2917–2922.
A. Kurek–Tyrlik et al. Ann./Recl. No. 9, 1997 pp. 1997–2001.

*Primary Examiner*—Kathleen K. Fonda
*Attorney, Agent, or Firm*—George W. Johnston; Patricia S. Rocha-Tramaloni; Robert A. Silverman

[57] ABSTRACT

This invention provides a method of treating or preventing neoplastic diseases. The method comprises adminstering to a host in need of such treatment or prevention an effective amount of a Vitamin $D_3$ analog of the Formula I

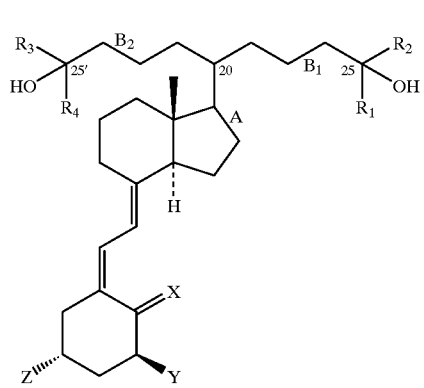

wherein:
  X is $H_2$ or $CH_2$;
  Y is hydrogen, hydroxy or fluorine;
  Z is hydroxy;
  $R_1$ and $R_2$ are a $(C_1-C_4)$ alkyl or fluoroalkyl, or $R_1$ and $R_2$ together with $C_{25}$ form a $(C_3-C_6)$ cycloalkyl or cyclofluoroalkyl;
  $R_3$ and $R_4$ are a $(C_1-C_4)$ alkyl or fluoroalkyl, or $R_3$ and $R_4$ together with $C_{25'}$ form a $(C_3-C_6)$ cycloalkyl or cyclofluoroalkyl;
  A is a single bond or a double bond;
  $B_1$ is a single bond, an E-double bond, a Z-double bond or a triple bond; and
  $B_2$ is a single bond, an E-double bond, a Z-double bond or a triple bond; or a prodrug thereof.

15 Claims, No Drawings

METHOD OF USING VITAMIN $D_3$ ANALOGS WITH BIS C-20 SIDE CHAINS

This application claims benefit under 35 U.S.C. § 119(e) of provisional applications 60/044,981 filed Apr. 28, 1997, and 60/072,182 filed Jan. 22, 1998.

BACKGROUND OF THE INVENTION

1. Field of the Invention

This invention relates to methods of treating or preventing neoplastic diseases using Vitamin $D_3$ analogs.

2. Description of Related Art a. Osteoporosis

Osteoporosis is the most common form of metabolic bone disease and may be considered the symptomatic, fracture stage of bone loss (osteopenia). Although osteoporosis may occur secondary to a number of underlying diseases, 90% of all cases appear to be idiopathic. Postmenopausal women are at risk for idiopathic osteoporosis (postmenopausal or Type I osteoporosis); another particularly high risk group for idiopathic osteoporosis is the elderly of either sex (senile or Type II osteoporosis). Osteoporosis has also been related to corticostercid use, immobilization or extended bed rest, alcoholism, diabetes, gonadotoxic chemotherapy, hyperprolactinemia, anorexia nervosa, primary and secondary amenor-rhea, transplant immunosuppression, and oophorectomy. Postmenopausal osteoporosis is characterized by fractures of the spine, while femoral neck fractures are the dominant features of senile osteoporosis.

The mechanism by which bone is lost in osteoporotics is believed to involve an imbalance in the process by which the skeleton renews itself. This process has been termed bone remodeling. It occurs in a series of discrete pockets of activity. These pockets appear spontaneously within the bone matrix on a given bone surface as a site of bone resorption. Osteoclasts (bone dissolving or resorbing cells) are responsible for the resorption of a portion of bone of generally constant dimension. This resorption process is followed by the appearance of osteoblasts (bone forming cells) which then refill with new bone the cavity left by the osteoclasts.

In a healthy adult subject, osteoclasts and osteoblasts function so that bone formation and bone resorption are in balance. However, in osteoporotics an imbalance in the bone remodeling process develops which results in bone being replaced at a slower rate than it is being lost. Although this imbalance occurs to some extent in most individuals as they age, it is much more severe and occurs at a younger age in postmenopausal osteoporotics, following oophorectomy, or in iatrogenic situations such as those resulting from corticosteroid therapy or the immunosuppression practiced in organ transplantation.

Various approaches have been suggested for increasing bone mass in humans afflicted with osteoporosis, including administration of androgens, fluoride salts, and parathyroid hormone and modified versions of parathyroid hormone. It has also been suggested that bisphosphonates, calcitonin, calcium, 1,25-dihydroxy vitamin $D_3$ and some of its analogs, and/or estrogens, alone or in combination, may be useful for preserving existing bone mass.

Vitamin $D_3$ is a critical element in the metabolism of calcium, promoting intestinal absorption of calcium and phosphorus, maintaining adequate serum levels of calcium and phosphorus, and stimulating flux of calcium into and out of bone. Vitamin $D_3$ is hydroxylated in vivo, with the resulting 1α, 25-dihydroxy metabolite being the active material. Animal studies with 1,25-$(OH)_2$ vitamin $D_3$ have suggested bone anabolic activity. Aerssens et al. in *Calcif Tissue Int*, 55: 443–450 (1994) reported upon the effect of 1α-hydroxy Vitamin $D_3$ on bone strength and composition in growing rats with and without corticosteroid treatment. However, human usage is restricted to antiresorption due to the poor therapeutic ratio (hypercalciuria and hypercalcemia as well as nephrotoxicity).

Dechant and Goa, in "Calcitriol. A review of its use in the treatment of postmenopausal osteoporosis and its potential in corticosteroid-induced osteoporosis", Drugs Aging [NEW ZEALAND 5 (4): 300–17 (1994)], reported that 1,25-dihydroxyvitamin $D_3$ (calcitriol) has shown efficacy in the treatment of postmenopausal osteoporosis (and promise in corticosteroid-induced osteoporosis) based upon a clinical trial in 622 women with postmenopausal osteoporosis. Patients with mild to moderate disease (but not those with more severe disease) who received calcitriol (0.25 microgram twice daily) had a significant 3-fold lower rate of new vertebral fractures after 3 years of treatment compared with patients receiving elemental calcium 1000 mg/day. In patients commencing long term treatment with prednisone or prednisolone, calcitriol 0.5 to 1.0 micrograms/day plus calcium 1000 mg/day, administered with or without intranasal calcitonin 400 IU/day, prevented steroid-induced bone loss. Overall, calcitriol was well tolerated. At recommended dosages hypercalcaemia was infrequent and mild, generally responding to reductions in calcium intake and/or calcitriol dosage. However, the narrow therapeutic window of calcitriol required that its use be adequately supervised, with periodic monitoring of serum calcium and creatinine levels. This study clearly identifies the key limitation of calcitriol therapy as the close proximity of therapeutic and toxic doses.

Baggiolini et al. in European Patent Publication No. 580,968 disclose fluorinated vitamin D3 analogs, including 1α-fluoro-25-hydroxy-16-ene-23-yne-26,27-hexafluorocholecalciferol, useful for the treatment of hyperproliferative disorders of the skin, for the treatment of cancer and leukemia, and for the treatment of sebaceous gland diseases. U.S. patent application Ser. No. 08/560,080 discloses and claims the use of this compound for the restoration of bone mass and/or density in osteoporosis. Pending U.S. patent application, Ser. No. 60/018,219 and U.S. patent application, "Fluorinated Vitamin $D_3$ analogs," filed Mar. 19, 1997 also discloses the use of certain vitamin $D_3$ analogs for the treatment of osteoporosis.

The vitamin $D_3$ analogs bearing two side chains attached to $C_{20}$ disclosed herein have not previously been described, nor has their use in the treatment of osteoporosis been recognized.

b. Hyperparathyroidism

Secondary hyperparathyroidism is a common finding in patients with chronic renal failure. It is established that the reduction of renal 1,25$(OH)_2$ vitamin $D_3$ (calcitriol) synthesis is one of the principal mechanisms leading to the secondary hyperparathyroidism in these patients and it has been shown that calcitriol possesses direct suppressive action on PTH synthesis. Therefore, administration of calcitriol has been recommended for the treatment of secondary hyperparathyroidism in these patients. However, as described above, calcitriol has potent hypercalcemic effects giving it a narrow therapeutic window which limits its usage, especially at high doses. It would therefore be desirable to have an alternative means of treating hyperparathyroidism without incurring these undesirable hypercalcemic effects.

The vitamin $D_3$ analogs bearing two side chains attached to $C_{20}$ disclosed herein have not previously been described, nor has their use in the treatment of hyperparathyroidism been recognized.

c. Leukemia and Cancer

Epidemiologic studies have correlated sun or UV light exposure with a lower incidence of a variety of malignancies, including breast, colon and prostate cancer. Evidence from receptor studies demonstrates that besides the classic target organs, such as intestine, kidney and bone, vitamin D receptors (VDR) are present on a wide variety of human normal and cancer cell lines and fresh tissue. Growth inhibition with vitamin D or 1,25-dihydroxycholecalciferol does not always translate into potential therapeutic efficacy in vivo. Early in vivo studies have focused on the anti-proliferative effects of 1,25-dihydroxycholecalciferol and its analogues in murine leukemia model systems where 1,25-dihydroxycholecalciferol has been shown to induce not only an anti-proliferative effect, but also a differentiating effect. Therapeutic efficacy in vivo has its limitations due to the hypercalcemia observed with high dose treatment of the parent 1,25-dihydroxycholecalciferol. As a result, a number of analogues have been developed that produce significant anti-tumor effects without hypercalcemia.

The vitamin $D_3$ analogs bearing two side chains attached to $C_{20}$ disclosed herein have not previously been described, nor has their use in the treatment or prevention of leukemia and cancer been recognized.

SUMMARY OF THE INVENTION

This invention provides a method of treating or preventing neoplastic diseases comprising administering to a host in need of such treatment or prevention an effective amount of a Vitamin $D_3$ analog of the Formula I

I wherein:

X is $H_2$ or $CH_2$;

Y is hydrogen, hydroxy or fluorine;

Z is hydroxy;

$R_1$ and $R_2$ are a $(C_1-C_4)$ alkyl or fluoroalkyl, or $R_1$ and $R_2$ together with $C_{25}$ form a $(C_3-C_6)$ cycloalkyl or cyclofluoroalkyl;

$R_3$ and $R_4$ are a $(C_1-C_4)$ alkyl or fluoroalkyl, or $R_3$ and $R_4$ together with $C_{25'}$ form a $(C_3-C_6)$cycloalkyl or cyclofluoroalkyl;

A is a single bond or a double bond;

$B_1$ is a single bond, an E-double bond, a Z-double bond or a triple bond; and $B_2$ is a single bond, an E-double bond, a Z-double bond or a triple bond.

This invention also provides a method of treating or preventing neoplastic diseases comprising administering to a host in need of such treatment or prevention an effective amount of a prodrug of a Vitamin $D_3$ analog of the Formula I

DETAILED DESCRIPTION OF THE INVENTION

Definitions

As used herein, the term $(C_1-C_4)$ alkyl means a linear fully-saturated hydrocarbon radical having one to four carbon atoms or a branched fully saturated hydrocarbon radical having three to four carbon atoms; a $(C_1C_4)$ fluoroalkyl is an alkyl radical, as defined above, in which one or more hydrogen atoms attached to the carbon backbone have been substituted with one or more fluorine atoms.

As used herein, the term $(C_3-C_6)$ cycloalkyl means a fully saturated cyclic hydrocarbon radical of three to six ring carbon atoms, e.g., cyclopropyl, cyclopentyl and the like; the term $(C_3-C_6)$ cyclofluoroalkyl is a cycloalkyl radical, as defined above, in which one or more hydrogen atoms attached to the carbon backbone have been substituted with one or more fluorine atoms.

As used herein, the term "E" denotes a stereochemical configuration about a carbon-carbon double bond such that the two hydrogen atoms are attached to different carbon atoms and are on opposite sides of the carbon—carbon double bond; the term "Z" denotes a stereochemical configuration about a carbon-carbon double bond such that the two hydrogen atoms are attached to different carbon atoms and are on the same side of the carbon-carbon double bond.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy group in compound (I) is bonded to any group that may be cleaved in vivo to regenerate the free hydroxyl group. Examples of prodrugs include, but are not limited to esters (e.g., acetate, formate, and benzoate derivatives), carbamates (e.g., N,N-dimethylaminocarbonyl) and ethers of hydroxy functional groups in compounds of Formula (I), and the like. Such compounds are routinely made by one of skill in the art by acylating or etherifying the hydroxy group in the parent molecule.

An "effective amount" means the amount of a compound that, when administered to a mammal for treating or preventing a disease, is sufficient to effect such treatment or prevention for the disease. The "effective amount" will vary depending on the compound, the disease and its severity and the age, weight, etc., of the mammal to be treated.

General Synthetic Scheme

Compounds of this invention may generally be prepared by reaction and combination of fragments of Vitamin $D_3$ molecules. In this regard, the synthetic processes described in Shiuey et al., *J. Org. Chem*, 55: 243 (1990) may be used to prepare and combine the Vitamin $D_3$ fragments. The preparation of compounds of Formula I and intermediates in its preparation is illustrated by the following Reaction Schemes.

Compounds of Formula I are prepared from compounds of Formula II,

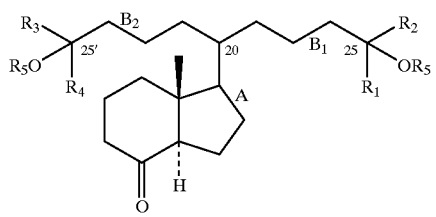

II where $R_1$, $R_2$, $R_3$, $R_4$, A, $B_1$ and $B_2$ are described above, and $R_5$ is hydrogen or trimethylsilyl, by reaction with compounds of Formula III,

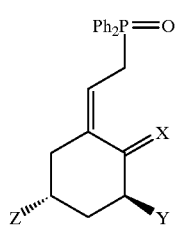

III where X is described above, Y is hydrogen, fluorine or tert-butyldimethyl-silyloxy group, and Z is a tertiary butyl-dimethyl-silyloxy group, followed by removal of the silyl protecting groups.

In general, a compound of Formula III is reacted with n-butyllithium and a compound of Formula II in a mixture of hexane and tetrahydrofuran at a temperature of -78° C. to give a compound of Formula I after removal of silyl protecting groups wit-h tetrabutylammonium fluoride in tetrahydrofuran solvent.

It should be noted that although the shown intermediates have hydroxy groups typically protected as silylethers, the scope of the invention includes the use of alternative hydroxyl protecting groups known in the art as described in T. W. Greene, "Protective Groups in Organic Synthesis," Wiley, New York (1991) and J. F. McOmie, "Protective Groups in Organic Chemistry," Plenum Press, London (1973) together with alternative methods for deprotection.

Synthesis and purification of compounds of Formula III are known and conventional in this art. See, for example, U.S. Pat. Nos. 5,086, 191 and 5,616,759 to DeLuca et al., 5,087,619 to Baggiolini et al., 5,384,314 to Doran et al., 5,428,029 to Doran et al., 5,451,574 to Baggiolini et al.; European Patent Application EP 0 808 832; patent publication WO 96/31216 to Brasitus et al.; Shiuey et al., *J. Org. Chem.*, 55: 243–247 (1990), Kiegel, J. et al. and *Tetr. Lett.*, 32: 6057–6060 (1991), Perlman, K. L., et al., *Tetr. Lett.*, 32: 7663–7666 (1991).

Reaction Scheme 1 shows a procedure for preparing a compound of Formula Ia where $B_1$ and $B_2$ are single bonds; $R_1$–$R_4$ are each $CH_3$; X $CH_2$; and Y and Z are OH.

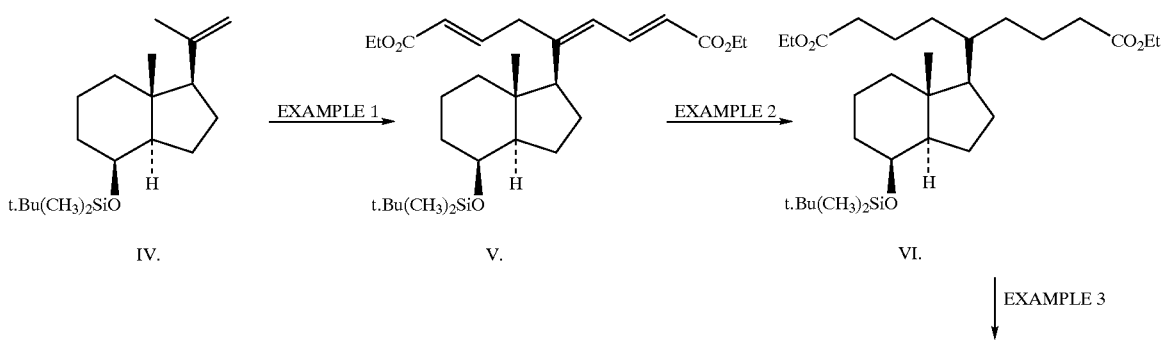

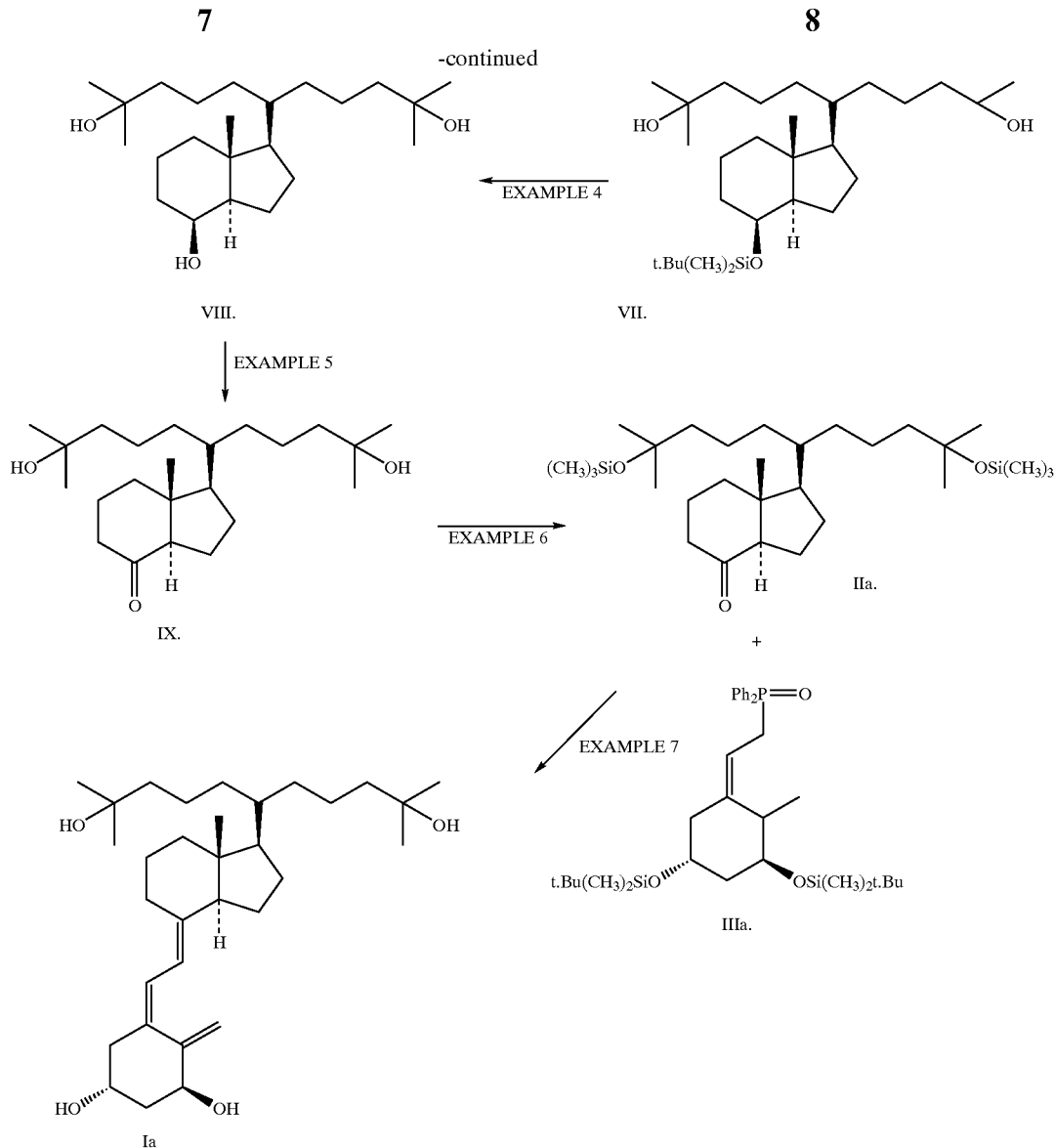

In Reaction Scheme 1, the compound of Formula IV is a known compound prepared by dehydration of the corresponding precursor alcohol. See, for example, Wovkulich, P. M. et al., *Tetrahedron*, 40: 2283 (1984). The compound of Formula IV is converted to the compound of Formula V by reaction with ethyl propiolate in the presence of a Lewis acid, such as ethylaluminum dichloride. The reaction is conducted in a chlorinated hydrocarbon solvent such as dichloromethane, at room temperature. The compound of Formula V is converted to the compound of Formula VI by hydrogenation in the presence of a catalyst such as 10% palladium on carbon. The reaction is conducted in an ester solvent such as ethyl acetate, at one atmosphere pressure, at room temperature. The compound of the Formula VI is converted to the compound of Formula VII by reaction with methylmagnesium bromide in an ether solvent such as mixture of diethylether and tetrahydrofuran, at room temperature. The compound of Formula VII is converted to the compound of the Formula VIII by reaction with aqueous 30% fluorosilicic acid, in a mixture of acetonitrile and tetrahydrofuran as solvent, at room temperature. The compound of Formula VIII is oxidized to the compound of Formula IX with pyridinium dichromate in a chlorinated hydrocarbon solvent, such as dichloromethane, at room temperature. The compound of Formula IX is reacted with trimethyl-silylimidazole in dichloromethane as a solvent to give the compound of Formula IIa. The compound of Formula IIIa is reacted with n-butyllithium and the compound of Formula IIa in a mixture of hexane and tetrahydrofuran at a temperature of −78° C. to give the compound of Formula Ia after removal of silyl protecting groups with tetrabutylammonium fluoride in tetrahydrofuran solvent.

Compounds of Formula I where A is a single bond or a double bond and $B_1$ and $B_2$ are double and triple bonds are prepared by reacting the corresponding precursors analogous to Formula II with compounds of Formula III. The corresponding precursors analogous to Formula II are prepared by methods known to one of skill in the art. Exemplary synthetic routes are shown in Reaction Scheme 2.

SCHEME 2

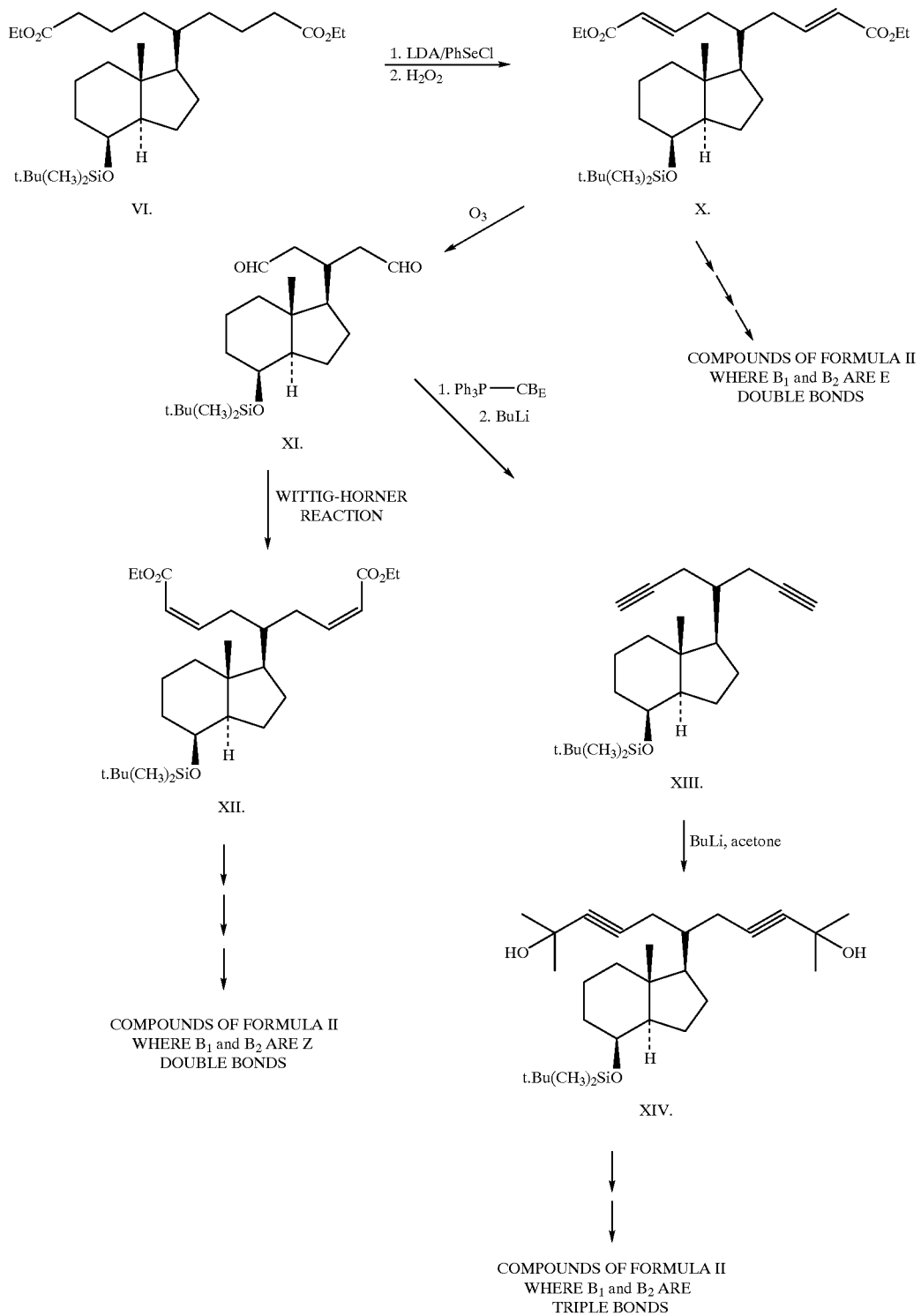

Compounds of Formula II where $B_1$ and $B_2$ are trans double bonds (E) are prepared by converting the compound of Formula VI to the corresponding bis-unsaturated ester X by treatment with lithium diisopropylamide and phenylselenylchloride followed by hydrogen peroxide oxidation and selenoxide elimination. This bis-unsaturated ester X is converted to the precursor analogous to IIa in which $B_1$ and $B_2$ are trans double bonds (E) by reactions as shown in Scheme 1.

Compounds of Formula II where $B_1$ and $B_2$ are cis double bonds (Z) may be obtained by oxidative cleavage of the double bond of compounds of Formula X with reagents such as ozone or osmium tetroxide/sodium metaperiodate to produce an aldehyde of Formula XI. The aldehyde XI is then condensed using the Still modification of the Wittig-Horner reaction with a phosphonate ylide $(CF_3CH_2O)_2P(O)CH_2C(O)OEt$ to give a bis-unsaturated ester XII in which the double bond is stereospecifically cis (Z). This bis-unsaturated ester XII is converted to the precursor analogous to IIa in which $B_1$ and $B_2$ are cis double bonds (Z) by reactions as shown in Scheme 1.

Compounds of Formula II where $B_1$ and $B_2$ are triple bonds can be prepared by dehydrogenating the unsaturated esters of Formula X or XII to the corresponding triple bond containing ester followed by condensation with an organometallic reagent as shown in Reaction Scheme 1 to give a compound analogous to that of Formula Ia. Formation of the triple bond may also be accomplished by bromination/dehydrobromination of the double bond in compounds of Formula X and XII. Alternatively, the aldehyde of Formula XI can be treated with butyllithium and triphenylphosphine/carbon tetrabromide using the Corey-Fuchs reaction to generate acetylide anion XIII which is condensed with a ketone to produce the corresponding acetylenic alcohol XIV analogous to VII.

Similarly, starting from the analog of Compound VI where A is a double bond, one can obtain the precursor analogous to IIa where A is a double bond.

Compounds of Formula II with varying alkyl and fluoroalkyl groups $R_1 14 R_4$ may be prepared by condensing the appropriate organometallic reagent e.g., an alkyllithium or Grignard reagent with a C-25 ester as in V, VI, X and XII. Alternatively, these groups may be introduced by condensing an acetylide anion derived from an intermediate such as XIII with an appropriate ketone or fluoroketone (e.g. hexafluoroacetone).

Preferred Embodiments

In certain preferred embodiments, $B_1$ and $B_2$ are double bonds or triple bonds.

In other preferred embodiments, A is a double bond.

In other preferred embodiments, A is a single bond.

Preferred embodiments also include those in which X is $CH_2$ and Y is fluoro or hydroxy.

Other preferred embodiments are those where $R_1$–$R_4$ are alkyl or fluoroalkyl, preferably trifluoromethyl.

Another aspect of the invention includes prodrugs of a compound of Formula I.

A number of different substituent preferences have been given above and following any of these substituent preferences results in a compound of the invention that is more preferred than one in which the particular substituent preference is not followed. However, these substituent preferences are generally independent, although some preferences are mutually exclusive, and following more than one of these preferences may result in a more preferred compound than one in which fewer of the substituent preferences are followed.

Utility

The compounds of this invention are useful for the prevention and treatment of a variety of mammalian conditions manifested by loss of bone mass. In particular, the compounds of this invention are indicated for the prophylaxis and therapeutic treatment of osteoporosis and osteopenia in mammals without inducing hypercalciuria, hypercalcemia, or nephrotoxicity. As used herein, "hypercalciuria" is excessive calcium in the urine, in humans corresponding to an excretion of greater than 4 mg/kg/day. This often results in nephrolithiasis (renal calculi). "Hypercalcemia" is an excessive concentration of calcium in the serum; in humans (and rats) this corresponds to greater than about 10.5 mg/dl. "Intolerable hypercalcemia", usually occurring at serum calcium concentrations greater than about 12 mg/dl, is associated with emotional lability, confusion, delirium, psychosis, stupor, and coma.

The compounds of this invention are expected to be useful in the treatment of Type I (postmenopausal), Type II (senile), and Type III (iatrogenic) osteoporosis, including that associated with immunosuppressive drugs used in organ transplantation, as well in the treatment of osteodystrophy due to renal dialysis and hyperparathyroidism.

Compounds of this invention are also useful in treating diseases caused by elevated levels of parathyroid hormone. In one aspect, compounds of the invention are used in treating secondary hyperparathyroidism associated with renal failure and in particular with reversing or reducing the bone loss associated with renal insufficiency. Other aspects include the treatment of renal osteodystrophy associated with late stage secondary hyperparathyroidism. Other aspects include the treatment of primary hyperparathyroidism.

Compounds of Formula I are also useful in treating or preventing neoplastic diseases. Examples of neoplatic diseases include, without limitation, leukemia, colon cancer, breast cancer and prostate cancer.

Compounds of Formula I are also useful in treating immunosuppressive and autoimmune diseases. Such diseases include, but are not limited to, multiple sclerosis, systemic lupus erythematosus, diabetes, thyroiditis and allograft rejection. In particular, compounds of Formula I are useful to to treat diseases via modulation of the activity of the vitamin $D_3$ receptor (VDR). The utility of these compounds is demonstrated in vivo using murine models for these diseases as its well known in the art. See, e.g., Lemire et al., *Autoimmunity*, 12: 143–148 (1992); Lemire et. al., *J. Clin. Invest.*, 87: 1103–1107 (1991), Lemire et al., *Endocrinology*, 135: 2818 (1994), and Lemire et al., *J. Cellular Biochem.*, 49: 26–31 (1992).

Generally, compounds of this invention do not cause the elevated calcium levels observed with other vitamin $D_3$ analogs such as 1,25 $(OH)_2$ vitamin $D_3$, thus providing an improved therapeutic ratio and better treatment of the above diseases.

Administration & Pharmaceutical Compositions

In general, the compound of this invention may be administered in amounts between about 0.0002 and 0.5 mg compound/kg body weight per day, preferably from about 0.001 to about 0.1 mg/kg body weight per day, most preferably from about 0.002 to about 0.02 mg/kg body weight per day. For a 50 kg human subject., the daily dose of active ingredient may be from about 0.01 to about 25 µgs. preferably from about 0.05 to about 10 µgs, most preferably from about 1.0 µg to about 10 µg per day. This dosage may be delivered in a conventional pharmaceutical composition by a single administration, by multiple applications, or via controlled release, as needed to achieve the most effective results, preferably once or twice daily by mouth. In certain situations, alternate day dosing may prove adequate to achieve the desired therapeutic response.

The selection of the exact dose and composition and the most appropriate delivery regimen will be influenced by, inter alia, the pharmacological properties of the formulation, the nature and severity of the condition being treated, and the physical condition and mental acuity of the recipient. In the treatment of corticosteroid induced osteopenia, it is expected that the requisite dose will be greater for higher doses of corticosteroids.

Representative delivery regimens include oral, parenteral (including subcutaneous, intramuscular and intravenous), rectal, buccal (including sublingual), pulmonary, transdermal, and intranasal, most preferably oral. Administration may be continuous or intermittent (e.g., by bolus injection).

A further aspect of the present invention relates to pharmaceutical compositions comprising as an active ingredient a compound of the present invention, in admixture with a pharmaceutically acceptable, non-toxic carrier. As mentioned above, such compositions may be prepared for parenteral (subcutaneous, intramuscular or intravenous) administration, particularly in the form of liquid solutions or suspensions; for oral or buccal administration, particularly in the form of tablets or capsules; for pulmonary or intranasal administration, particularly in the form of powders, nasal drops or aerosols; and for rectal or transdermal administration.

The compositions may conveniently be administered in unit dosage form and may be prepared by any of the methods well-known in the pharmaceutical art, for example as described in *Remington's Pharmaceutical Sciences,* 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Orally administrable compositions may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethylcellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Preferred solid oral dosage forms include tablets, two-piece hard shell capsules and soft elastic gelatin (SEG) capsules. SEG capsules are of particular interest because they provide distinct advantages over the other two forms (see Seager, H., "Soft gelatin capsules: a solution to many tableting problems"; *Pharmaceutical Technology,* 9, (1985). Some of the advantages of using SEG capsules are: a) dose-content uniformity is optimized in SEG capsules because the drug is dissolved or dispersed in a liquid that can be dosed into the capsules accurately b) drugs formulated as SEG capsules show good bioavailability because the drug is dissolved, solubilized or dispersed in an aqueous-miscible or oily liquid and therefore when released in the body the solutions dissolve or are emulsified to produce drug dispersions of high surface area and c) degradation of drugs that are sensitive to oxidation during long-term storage is prevented because the dry shell of soft gelatin provides a barrier against the diffusion of oxygen.

The dry shell formulation typically comprises of about 40% to 60% concentration of gelatin, about a 20% to 30% concentration of plasticizer (such as glycerin, sorbitol or propylene glycol) and about a 30 to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

The following examples are given to enable those skilled in the art to more clearly understand and to practice the present invention. They should not be considered as limiting the scope of the invention, but merely as being illustrative and representative thereof.

EXPERIMENTAL

EXAMPLE 1

[1R-[1α(2E,4E,7E),3aβ,4α,7aα]]-5-[4-[[(1,1-dimethylethyl) dimethylsilyl]oxy] Octahydro-7a-methyl-1H-inden-1-yl]-2,4,7-nonatrienedioic acid diethyl ester (V).

To a stirred solution of 3.08 g (10.0 mmol) of [1R-(1α, 3aβ,4α,7aα)]-(1,1 -dimethylethyl)dimethyl[[octahydro-7a-methyl-1-(1 -methylethenyl)-1H-inden-4-yl] oxy]silane and 3.92 g (40.0 mmol) of ethyl propiolate in 20 mL of dichloromethane was added 40 mL (40.0 mmol) of a 1.0 M solution of ethylaluminum dichloride in hexanes. The mixture was stirred under argon at room temperature for 24 hrs, treated with 981 mg (10 mmol) of ethyl propiolate and 7.5 mL (7.5 mmol) of a 1.0 M solution of ethylaluminum dichloride in hexanes; and stirred for an additional 18 hrs. The resultant orange-red solution was added portion-wise to a mixture of 200 mL ethyl acetate and 100 mL of 50% brine, and, after the fizzing had subsided, the organic phase was collected and the aqueous phase was re-extracted with 3×100 mL of ethyl acetate. The combined organic extracts were washed with 2×100 mL of 50% brine, dried ($Na_2SO_4$), and evaporated to give 5.76 g of a reddish gum, which was subjected to flash chromatography on 120 g of silica gel (40–65 μm mesh, 3.5 cm diameter column) with 10% ethyl acetate in hexanes as eluent, collecting 20-mL fractions. Fractions 21–32 were combined and evaporated to give 2.18g of crude product. Further purification was achieved by HPLC (15–30 μm mesh silica gel, 50 cm ×50 mm column, flow rate of 70 mL/min) with 7.5% ethyl acetate in hexanes as eluent to give 1.62 g (32%) of the titled compound, $R_T$ 25 minutes, as a pale yellow gum: $[\alpha]^{25}D+83.50°$ (EtOH, c=0.98); UV (MeOH) 284 (ε=28,173), 207 (ε=16,884) nm; IR ($CHCl_3$) 1708, 1651, 1628 $cm^{-1}$; $^1H$ NMR ($CDCl_3$) δ0.006 (6 H, s), 0.80, 3 H, s), 0.88 (9 H, s), 1.16 (1 H, t, J=7.6 Hz), 1.28 (6 H, overlapping t, J=7 Hz), 1.67–1.78, (6 H, m), 2.16 (1 H, t, J=9 Hz), 3. 00, (1 H, dd, J=6, 16, Hz), 3.35 (1 H, dd, J=16, 4 Hz), 4.02 (1 H, s), 4.16 (4 H, overlapping q, J=7 Hz), 5.75 (1 H, d, J=16Hz), 5.84(1 H, d, J=15 Hz), 6.17 (1 H, d, J=11 Hz), 6.88 (1 H, dt, J=16, 6 Hz), 7.50 (1 H, dd, J=11, 15, Hz); MS (EI) m/z 504 ($M^+$, 23).

Anal. Calcd for $C_{29}H_{48}O_5Si$: C, 69.00; H, 9.58; Si, 5.56. Found: C, 68.94; H, 9.69; Si, 5.67.

EXAMPLE 2

[1R-(1α,3aβ,4α,7aα)]-5-[4-[[(1,1-dimethylethyl) dimethylsilyl]oxy]Octahydro-7a-methyl-1H-inden-1-yl]nonanedioic acid diethyl ester (VI).

A stirred solution of 1.009 g (2.0 mmol) of [1R-[1α(2E, 4E,7E),3aβ,4α,7aα]]-5-[4-[[(1,1-dimethylethyl)

dimethylsilyl]oxy]octahydro-7a-methyl-1H-inden-1-yl]-2, 4,7-nonatrienedioic acid diethyl ester in 50 mL of ethyl acetate was hydrogenated over 200 mg of 10% palladium on charcoal at room temperature and atmospheric pressure until hydrogen absorption ceased (140 mL of hydrogen was absorbed during 2.5 hrs). The mixture was filtered over a pad of Celite, which was washed with 4×50 mL of ethyl acetate, and the combined filtrate and washings were evaporated to give 1.07 g of a colorless oil. This was purified by flash chromatography on 60 g of silica gel (40–65 μm mesh, 3.5 cm diameter column) with 12% ethyl acetate in hexanes as eluent, collecting 20-mL fractions. Fractions 7–12 were combined and evaporated to give 964 mg (94%) of the titled compound as a colorless oil: $[\alpha]D^{25}$+32.1° ($CHCl_3$, c=1.04); IR ($CHCl_3$) 1726 $cm^{-1}$; $^1H$ NMR ($CDCl_3$) δ0.00 (3 H, s), 0.01 (3 H, s), 0.87 (9 H, s), 0.88 (3 H, s), 1.27 (6 H, t, J=7 Hz), 1.28–190 (21 H, m), 2.25 (4 H, br t), 3.98 (1 H, s), 4.11 (4 H, q, J=7 Hz); MS (FAB) m/z 511 ($M^+$+1, 100).

Anal. Calcd for $C_{29}H_{54}O_5Si$: C, 68.11; H, 10.66; Si, 5.50. Found: C, 68.21; H, 10.85; Si, 5.43.

EXAMPLE 3

[1R-(1α,3aβ,4α,7aα]-6-[4-[[(1,1-dimethylethyl) dimethylsilyl]oxy]Octahydro-7a-methyl-1H-inden-1-yl]-2,10-dimethyl-2,10-undecanediol (VII).

To a stirred solution of 868 mg (1.7 mmol) of [1R-(1α, 3aβ,4α,7aα)]-5-[4-[[(1,1-dimethylethyl)dimethylsilyl]oxy] octahydro-7a-methyl-1H-inden-1-yl]nonanedioic acid diethyl ester in 12 mL of anhydrous THF was added dropwise, with cooling (ice bath), 5.0 mL (15 mmol) of a 3.0 M solution of methylmagnesium bromide in ether. The mixture was stirred at room temperature for 45 minutes, cooled to 5° C., and quenched by the dropwise addition of 3.0 mL of saturated $NH_4Cl$. After the fizzing had subsided, 15 mL of ethyl acetate and 15 mL of saturated $NH_4Cl$ were added, stirring was continued for 20 minutes, and the mixture was poured into 100 mL of ethyl acetate and 50 mL of saturated $NH_4Cl$. The organic phase was collected and the aqueous phase was re-extracted with 3×60 mL of ethyl acetate. The combined organic extracts were washed with 2×100 mL of 50% brine, dried ($Na_2SO_4$), and evaporated to give 814 mg of a colorless gum, which was purified by flash chromatography on 100 g of silica gel (40–65 μm mesh, 3.5 cm diameter column) with 50% ethyl acetate in hexanes as eluent taking 20-mL fractions. Fractions 19–20 were combined and evaporated to give, after high vacuum drying (17 hrs), 763 mg (93%) of the titled compound as a colorless foam: $[\alpha]D^{25}$+35.8° (EtOH, c=1.02); IR ($CHCl_3$) 3608 $cm^{-1}$; $^1H$ NMR ($CDCl_3$) δ0.00 (6 H, s), 0.88 (9 H, s), 0.90 (3 H, s), 1.20 (12 H, s), 1.23–1.90 (27 H, m), 3.99 (1 H, s); MS (EI) m/z 482 (3, $M^+$).

Anal. Calcd for $C_{29}H_{58}O_3Si$: C, 72.14; H, 12.11; Si, 5.82. Found: C, 72.18; H, 11.99; Si, 5.69.

EXAMPLE 4

[1S-(1α,3aβ,4α,7aα)]Octahydro-1-[5-hydroxy-1-(4-hydroxy-4-methylpentyl)-5-methylhexyl]-7a-methyl-4H-inden-4-ol. (VIII).

To a stirred solution of 700 mg (1.45 mmol) of [1R-(1α, 3aβ,4α,7aα)]-6-[4-[[(1,1-dimethylethyl)dimethylsilyl]oxy] octahydro-7a-methyl-1H-inden-1-yl]-2,10-dimethyl-2,10-undecanediol in 5 mL of THF and 15 mL of $CH_3CN$ contained in a Teflon bottle was added 3.0 mL of an approximately 30% aqueous solution of fluorosilicic acid (prepared according to A. S. Pilcher and P. DeShong, *J. Org. Chem.*, 1993, 58, 5130) and the mixture was stirred under argon at room temperature for 1.0 h. Four 2.0-mL portions of the fluorosilicic acid solution were then added at hourly intervals, for a total of 11 mL of reagent and a reaction time of 5 hrs. The reaction mixture was poured cautiously into a mixture of 125 mL of ethyl acetate and 75 mL of saturated aqueous $KHCO_3$ solution. After the fizzing had subsided, the organic phase was collected and the aqueous phase was re-extracted with 3×75 mL of ethyl acetate. The organic extracts were washed with 125 mL of 50% brine, dried ($Na_2SO4$), and evaporated to give 534 mg of a gum, which was purified by flash chromatography on 70 g of silica gel (40–65 μm mesh, 3.5 cm diameter column) with 70% ethyl acetate as eluent, taking 20-mL fractions. Fractions 17–30 were combined, filtered and evaporated, and the residue was kept under high vacuum for 4 hrs to give 458 mg (85%) of the titled compound as a colorless foam: $[\alpha]D^{25}$+26.2° ($CHCl_3$, c=0.76); IR ($CHCl_3$) 3608 $cm^{-1}$; $^1H$ NMR ($CDCl_3$) δ0.9.3 (3 H, s), 1.21 (12 H, s), 1.24–1.60 (24 H, m), 1.79–1.95 (4 H, m), 4.07 (1H,s); MS (FAB) m/z 369 ($M^+$+H).

EXAMPLE 5

[1S-(1α,3aβ,7aα)]Octahydro-1-[5-hydroxy-1-(4-hydroxy-4-methylpentyl)-5-methylhexyl]-7a-methyl-4H-inden-4-one (IX).

To a stirred solution of 400 mg (1.08 mmol) of [1S-(1α, 3aβ,4α,7aα)]octahydro-1-[5-hydroxy-1-(4-hydroxy-4-methylpentyl)-5-methylhexyl]-7a-methyl-4H-inden-4-ol in 8.0 mL of dichloromethane was added 1.30 g (3.45 mmol) of pyridinium dichromate and the mixture was stirred at room temperature for 4.75 hrs. It was diluted with 20 mL of diisopropyl ether, stirred for a further 15 minutes and filtered over a pad of Celite. The Celite was washed with 4×40 mL of diisopropyl ether and the combined filtrate and washings were evaporated to give 405 mg of a pale yellow gum, which was purified by flash chromatography on 70 g of silica gel (40–65 μm mesh, 3.5 cm diameter column) with 75% ethyl acetate in hexanes as eluent taking 20-mL fractions. Fractions 17–30 were combined and evaporated to give a colorless gum, which was kept under high vacuum for 4.5 hrs to give 372 mg (94%) of the titled compound as a colorless gum: $[\alpha]D^{25}$0.45° (EtOH, c=0.92); IR ($CHCl_3$) 3608,1706 $cm^{-1}$; $^1H$ NMR ($CDCl_3$) δ0.63 (3 H, s), 1.22 (12 H, s), 1.30–2.10 (22 H, m), 2.20–2.28 (2 H, m), 2.45 (1 H, dd, J=7.6,11 Hz); MS m/z 348 ($M^+$–18).

EXAMPLE 6

[1S-(1α,3aβ,7aα)]Octahydro-7a-methyl-1-[5-methyl-1-[4-methyl-4-[(trimethylsilyl)oxy]pentyl]-5-[(trimethylsilyl)oxy]hexyl]-4H-inden-4-one (IIa).

To a stirred solution of 366.6 mg (1.0 mmol) of [1S-(1α, 3aβ,7aα)]octahydro-1-[5-hydroxy-1-(4-hydroxy-4-methylpentyl)-5-methylhexyl]-7a-methyl-4H-inden-4-one in 10.0 mL of dichloromethane was added 1.25 mL (8.5 mmol) of 1-(trimethylsilyl)imidazole and the mixture was stirred under argon at room temperature for 4.25 hrs. It was diluted with 7.0 mL of water, stirred for a further 15 minutes, and poured into a mixture of 75 mL of ethyl acetate and 50 mL of 50% brine. The organic phase was collected and the aqueous phase was re-extracted with 3×50 mL of ethyl acetate. The combined oraganic extracts were washed with 3×75 mL of 50% brine, dried ($Na_2SO_4$), and evaporated to give a colorless oil, which was purified by flash chromatography on 65 g of silica gel (40–65 μm mesh, 3.5 cm diameter column) with 20% ethyl acetate in hexanes as eluent, taking 20-mL fractions. Fractions 5–7 were combined, concentrated to ca. 5 mL, filtered through a 0.45 μm filter (Millex-HV) and evaporated to give a colorless oil, which was kept under high vacuum for 18 hrs to give 469 mg (91%) of the titled compound: $[\alpha]D^{25}$ –3.21° (CHCl$_3$, c=0.87); IR (CHCl$_3$); 1706 cm$^{-1}$; $^1$H NMR (CDCl$_3$) δ0.01 (18 H, s), 0.63 (3 H, s), 1.20 (6 H, s), 1.21 (6 H, s),1.26–1.49 (14 H, m), 1.50–2.10 (8 H, m 2.21–2.31 (2 H, m), 2.46 (1 H, dd, J=12,11 Hz); MS (EI) m/z 495 (M$^+$-15).

Anal. Calcd for $C_{29}H_{58}O_3Si_2$: C, 68.17; H, 11.44; Si, 10.99. Found: C, 68.19; H, 11.41; Si, 11.07.

EXAMPLE 7

(1α,3β,5Z,7E)-21-(3-hydroxy-3-methylbutyl)-9,10-Secocholesta-5,7,10, (19)-triene-1,3,25-triol (Ia).

To a stirred, cold (–78° C.) solution of 466 mg (0.8 mmol) of the reagent [3S-(1Z,3α,5β)]-[2-[3,5-bis[[(1,1-dimethylethyl)dimethylsilyl]oxy]-2-methylene-cyclohexylidene]ethyl]di-phenylphosphine oxide in 4.0 mL of anhydrous THF was added 0.5 mL of a 1.6 M solution of n-butyllithium in hexanes. The resultant deep red solution was stirred at –78° C. for 7 minutes, treated with 204 mg (0.40 mmol) of [1S-(1α,3aβ,7aα)]octahydro-7a-methyl-1-[5-methy-1-[4-methyl-4-[(trimethylsilyl)oxy]pentyl]-5-[(trimethylsilyl)oxy]hexyl]-4H-inden-4-one in 3.0 mL of anhydrous THF, and stirred at –78° C. for 3 hrs. The mixture was allowed to warm to room temperature, quenched with 5 mL of a 1:1 mixture of 2N Rochelle salt solution and 2N KHCO$_3$ solution, stirred for an additional 15 minutes, and poured into a mixture of 80 mL of ethyl acetate and 50 mL of 1:1 2N Rochelle salt solution and 2N KHCO$_3$ solution. The organic phase was collected and the aqueous phase was re-extracted with 3×60 mL of ethyl acetate. The combined organic extracts were washed with 3×75 mL of 50% brine, dried (Na$_2$SO$_4$) and evaporated to give 1.29 g of a gum, which was purified by flash chromatography on 60 g of silica gel (40–65 μm mesh; 3.5 cm diameter column) with 8% ethyl acetate in hexanes, taking 20-mL fractions. Fractions 5 and 6 were combined and evaporated to give 208 mg of a colorless gum. The latter was dissolved in 4.0 mL of THF, treated with 4.0 mL of a 1.0M solution of tetrabutylammonium fluoride in THF, and the solution was stirred under argon for 17 hrs. It was diluted with 5.0 mL of water, stirred for an additional 15 minutes, and poured into a mixture of 80 mL of 80% ethyl acetate in hexanes and 50 mL of water. The organic phase was collected and the aqueous phase was re-extracted with 4×80 mL of 80% ethyl acetate in hexanes. The combined organic extracts were washed with 4×80 mL of 50% brine, dried (Na$_2$SO$_4$), and evaporated to give 139 mg of a semi-solid, which was purified by flash chromatography on 60 g of silica gel (40–65 μm mesh; 3.5 cm diameter column) with 6% 2-propanol in ethyl acetate as eluent taking 20-mL fractions. Fractions 17–25 were combined and evaporated to give 108 mg of a colorless foam. This was further purified by HPLC (15–30 μm mesh silica gel, 50 cm × 50 mm column; flow rate of 70 mL/min) with 3% 2-propanol in ethyl acetate as eluent. The material eluting with an $R_T$ of 35 minutes was collected and the solvents were evaporated to give a colorless semi-solid. This was dissolved in 15 mL of anhydrous methyl formate, filtered through a 0.45 μm filter (Millex-HV), concentrated, and kept under high vacuum for 4 hrs to give 82 mg of the titled compound as a colorless, amorphous solid: $[\alpha]D^{25}$ +13.8° (EtOH, c=0.5); UV (MeOH) 263 (ε=17,545), 212 (ε=14, 702) nm; IR (CHCl$_3$) 3608 cm$^{-1}$; $^1$H NMR (CDCl$_3$) δ0.53 (3 H, s), 1.21 (12 H, s), 1.26–2.17 (32H, m), 2.30 (1 H, dd, J=10.7 Hz), 2.59(1 H, d, J=11 Hz), 2.83(1 H, d, J=13 Hz), 5.00(1 H, s), 5.33(1 H, s), 6.02 (1 H, d, J=11 Hz), 6.37 (1 H, d, J=11 Hz); HRMS (EI): Calcd for $C_{32}H_{54}O_2$: m/z 502.4022. Found m/z 502.4024.

EXAMPLE 8

21-(3-Hydroxy-3-methylbutyl)-1α-fluoro-25-hydroxy-cholecalciferol

To a stirred, cold (–78° C.) solution of 320 mg (0.67 mmol) of the reagent (S-trans-1-fluoro-5[[dimethyl(1,1-dimethylethyl)silyl]oxy-2-methenyl-3[diphenyl-phosphinyl)ethylidene]cyclohexane, in 4.0 mL of anhydrous THF was added 0.42 mL (0.67 mmol) of a 1.6 M solution of n-butyllithium in hexanes. The resultant deep red solution was stirred at –78° C. for 7 minutes, treated with 118 mg (0.23 mmol) of [1R-(1α,3aβ,7aα)]octahydro-7a-methyl-1-[5-methyl-1-[4-methyl-4[(trimethylsilyl)oxy]pentyl-5-[(trimethylsilyl)oxy]hexyl]-4H-inden-4-one in 2.0 mL of anhydrous THF, and stirred at –78° C. for 4.5 hours. The mixture was allowed to warm to room temperature, stirred for 20 minutes, and quenched with 5 mL of a 1:1 mixture of 1N Rochelle salt solution and 1N KHCO$_3$ solution. After 15 minutes, the mixture was poured into 50 mL of a 1:1 mixture of 1N Rochelle salt solution and 1N KHCO$_3$ solution. The organic phase was separated and the aqueous phase was re-extracted with 3×40 mL of ethyl acetate. The combined organic extracts were washed with 100 mL of 10% brine, dried (Na$_2$SO$_4$), and evaporated to give 426 mg of a colorless gum, which was purified by flash chromatography on 40 g of silica gel (40–65 μm mesh; 3.5 cm diameter column) with 5% ethyl acetate in hexanes as eluent, taking 15- mL fractions. Fractions 5–7 were combined and evaporated to give 144 mg of a colorless gum. The latter was dissolved in 3.0 mL of THF, treated with 2.0 mL of a 1.0 M solution of tetra-n-butylammonium fluoride in THF, and the solution was stirred under argon at room temperature for 17 hours. It was diluted with 5.0 mL of water, stirred for 10 minutes and poured into 50 mL of ethyl acetate and 40 mL of water. The organic phase was separated and the aqueous phase was re-extracted with 3×50 mL of ethyl acetate. The combined organic extracts were washed with 5×100 mL of water, dried (Na$_2$SO$_4$) and evaporated to give 78 mg of a gum, which was purified by flash chromatography on 40 g of silica gel (40–65 μm mesh; 3.5 cm diameter column) with 90% ethyl acetate in hexanes as eluent, taking 15-mL fractions. Fractions 14–20 were combined to give 57 mg of a colorless semi-solid, which was dissolved in 20 mL of anhydrous methyl formate and filtered through a 0.4 μm filter. The filtrate was concentrated to 1.0 mL, kept at 0° C. for 1.0 hour, and the crystals were collected by filtration to give 42 mg of the title compound, mp 96–98° C.; $[\alpha]D^{25}$ +38.6° (MeOH, c=0.5); UV (MeOH) 270 (ε=14,136), 242 (ε=14, 350), 210 (ε=13,564) nm; IR (CHCl$_3$) 3610 cm$^{-1}$; $^1$H NMR (CDCl$_3$) δ0.54 (3, H, s), 1.21 (12 H, s), 1.22–1.60 (21 H, m), 1.69 (2 H, m), 1.80 (1 H, m), 2.0 (3 H, m), 2.17 (1 m), 2.31 (1 H, m), 2.62 (1 H, d, J=12 Hz), 2.82 (1 H, d, J=12 Hz), 4.22 (1 H, br s), 5.07 (1 H, br t), 5.10 (1 H, s), 5.19 (1 H, br t), 5.39 (1H, s), 6.02 (1 H, d, J=11 Hz), 6.40 (1 H, d, J=11 Hz); MS (FAB) m/z 504.5 (M$^+$, 60).

EXAMPLE 9

21-(3-Hydroxy-3-methylbutyl)-1,25-dihydroxy-19-norcholecalciferol

To a stirred, cold (–78° C.) solution of 571 mg (1.0 mmol) of the reagent [3R,(3α,5β,Z)-3,5-bis [[1,1-dimethylethyl)

dimethylsilyl]oxy]cyclohexlidene]ethyl]diphenylphosphine oxide, in 6.0 mL of anhydrous THF was added 0.65 mL (1.04 mmol) of a 1.6 M solution of n-butyllithium in hexanes. The resultant deep red solution was stirred at −78° C. for 10 minutes, treated with 204.4 mg (0.4 nmol) of [1R-(1α,3β,7aα)]octahydro-7a-methyl-1-[5-methyl-1-[4-methyl-4[(trimethylsilyl)oxy]pentyl]-5-[(trimethylsilyl)oxy]hexyl]-4H-inden-4- one in 2.5 mL of anhydrous THF, and stirred at −78° C. for 3.0 hours. The mixture was allowed to warm to room temperature, stirred for 15 minutes and quenched with 15 mL of a 1:1 mixture of 1N Rochelle salt solution and 1N $KHCO_3$ solution. After 10 minutes, the mixture was poured into a mixture of 70 mL of ethyl acetate and 40 mL of a 1:1 mixture of 1N Rochelle salt solution and IN $KHCO_3$ solution. The organic phase was separated and the aqueous phase was re-extracted wtih 3×70 mL of ethyl acetate. The combined organic extracts were washed with 100 mL of 10% brine, dried ($Na_2SO_4$), and evaporated to give 760 mg of a colorless gum, which was purified by flash chromatography on 60 grams of silica gel (40–65 μm mesh; 3.5 cm diameter column) with 5% ethyl acetate in hexanes as eluent, taking 15 mL fractions. Fractions 5–10 were combined and evaporated to give 304 mg of a colorless gum. The latter was dissolved in 4.0 mL of THF, treated with 5.0 mL of a 1.0 M solution of tetra-n-butyllithium fluoride in THF, and the solution was stirred under argon at room temperature for 42 hours. It was diluted with 15 mL of water, stirred for 15 minutes, and poured into a mixture of 75 mL of ethyl acetate and 50 mL of 10% brine. The organic phase was separated and the aqueous phase was re-extracted with 3×70 mL of ethyl acetate. The combined organic extracts were washed with 5×100 mL of water, dried ($Na_2SO_4$), and evaporated to give 186 mg of a semi-solid, which was purified by flash chromatography on 50 g of silica gel (40–65 μm mesh; 3.5 cm diameter column) with 7.5% 2-propanol in ethyl acetate as eluent, taking 15-mL fractions. Fractions 11–29 were combined and evaporated. The residue was dissolved in 20 mL of anhydrous methyl formate and the solution was filtered through a 0.4 μm filter. Evaporation of the filtrate gave 154 mg of the title compound as a colorless solid: $[\alpha]D^{25}$ +50.93° (MeOH, c=0.32); $^1$H NMR ($CDCl_3$) δ0.54 (3, H, s), 1.21 (12 H, s), 1.2–2.0 (27 H, m), 2.20 (2 H, m), 2.48 (1 H,d, J=12 Hz), 2.25 (2 H, m), 2.82 (1 H 4.06 (1 H, br s) 4.10 (1 H, br s), 5.85 (1 H, d, J =12 Hz), 6.30 (1 H, d, J=Hz); MS (FAB) m/z 490.4 ($M^+$, 30).

EXAMPLE 10

EFFECT OF VITAMIN $D_3$ ANALOGS ON SECONDARY HYPERPARATHYROIDISM IN THE RAT RENAL INSUFFICIENCY MODEL

The parathyroid hormone suppressive activity of the vitamin $D_3$ analogs of this invention was demonstrated in rats with secondary hyper-parathyroidism due to renal failure using the 7/8 nephrectomy induced rat model of renal failure (*Kidney International*, M. Fukugawa et al., 39: 874–881 (1991).

Test Materials

Compound of Formula Ia $1,25(OH)_2$ vitamin $D_3$ (control)

Vehicle—Miglyol 812

Female Sprague Dawley rats were anesthesized, their right kidney removed and 2–3 branches of the left renal artery were ligated to achieve 7/8 nephrectomy. They were placed on a high phosphorous diet (0.6% Ca and 0.8 phosphorous). Approximately 3–6 weeks after surgery, rats were bled to screen serum PTH levels and rats with PTH levels between 100–500 pg/ml were selected for the study.

Rats were divided into five groups which were treated as shown in the Table below.

| Group | Number of rats | Treatment |
|---|---|---|
| 1 | 6 | Formula Ia, 10 μg/kg/day, po |
| 2 | 6 | Formula Ia, 1 μg/kg/day, po |
| 3 | 6 | Formula Ia, 0.1 μg/kg/day, po |
| 4 | 5 | $1,25(OH)_2$ vit. $D_3$, 0.2 μg/kg/day, po |
| 5 | 5 | Vehicle, po |

There was a pre-bleed (T=0) and each group was dosed daily for seven days by oral gavage with either the compound of Formula Ia (10, 1 or 0.1 μg/kg/day), vehicle control or $1,24(OH)_2$ vitamin $D_3$ positive control. Compounds were predissolved in ethanol and diluted with vehicle (Miglyol 812) followed by evaporation of the ethanol.

After the last day of dosing, the animals were bled again (T=1) and sacrificed. Serum PTH assays were done with Nichols Institute Diagnostic Kit #40-2240. Serum calcium assays were done with Sigma Diagnostic Kit #587 with o-cresophthaleiri. Serum creatinine assays were done with Sigma Diagnostic Kit #1600-320 with ammonium molybdate.

| Group | PTH pg/ml T = 1 - T = 0 | Final Ca Levels (mg/ml) |
|---|---|---|
| Formula Ia (10 μg/kg) | −132 | 11.97 |
| Formula Ia (1 μg/kg) | −124 | 10.35 |
| Formula Ia (0.1 μg/kg) | 112 | 10.20 |
| $1,25(OH)_2$ vit. $D_3$ (0.1 μg/kg) | −66 | 10.82 |
| Vehicle | 156 | 9.69 |

The results show that the compound of Formula Ia is more effective than $1,25(OH)_2$ vit. $D_3$ in suppressing the elevated levels of parathyroid hormone without causing elevated calcium levels.

EXAMPLE 11

Bone Anabolism in the Rat

Three month old rats are ovariectomized (Ovx) and administered either 1,25-dihydroxy vitamin $D_3$ (vit. D in Table) or one of the compounds of the present invention once a day by mouth starting at 3 weeks post-ovariectomy and continuing until final sacrifice at 6 weeks post-ovariectomy. Control groups, both sham (rats that were not ovariectomized) and Ovx, received vehicle only. Blood and urine samples were collected twice, at 4 weeks post-ovariectomy and again at the 6 week mark and the amount of serum and urine calcium was determined. The final femoral calcium determined upon sacrifice 6 weeks post-ovariectomy.

The bone mineral density of the right femur was determined by using a High Resolution Software Package on a QDR-1000W Bone Densitometer™ (Hologic, Waltham, Mass.). The animals were scanned by placing them on a scanning block in a supine position such that the right leg was perpendicular to the main body and the tibia was perpendicular to the femur.

The compounds of the present invention are more effective than 1,25-dihydroxy vitamin $D_3$ at bone accretion and do not induce hypercalciuria, nephrotoxicity, or hypercalcemia at therapeutically effective doses.

EXAMPLE 12

Autoimmunity in the Rat EAE Model

The ability of vitamin $D_3$ analogs to treat autoimmune diseases is demonstrated in vivo in the rat model of experimental autoimmune encephalomyelitis EAE).

Female Lewis rats are immunized with a 1:1 mixture of guinea pig spinal cord homogenate and modified Freund's complete adjuvant (4 mg/ml M. tuberculosis in incomplete Freund's adjuvant) via footpad injection. Compounds or vehicle is administered either subcutaneously or per os for 12 days starting on the 5th day after immunization. The animals are monitored for the onset of symptoms of EAE-loss of tail tonicity, weakness of hindlimbs, staggering gait, paralysis etc.

The compounds of Formula 1 are effective in reducing the symptoms of EAE in the rat model

EXAMPLE 13

Cell Proliferation Assay in MCF-7 Breast Cancer Cells

MCF-7 cells are human mammary carcinoma cells that are positive for estrogen receptors. The potential activity of vitamin $D_3$ analogs against breast cancer was assessed from inhibition of proliferation of MCF-7 cells in culture.

MCF-7 cells were plated at 5000 cells/well in 96-well plates and incubated at 37° C. in 5% $CO_2$/95% air in Dulbecco's Modified Eagle Medium containing 10% fetal bovine serum 700 nM insulin, 2 mM glutamine, 0.1 mM MEM non-essential amino acids and 1 mM sodium pyruvate. Stock solutions of vitamin $D_3$ analogs were prepared at a concentration of 10 mM in absolute ethanol and stored at −20° C. under argon. One day after plating, MCF-7 cells were refed with either control medium or medium containing varying concentrations of the vitamin $D_3$ analog. After a further 7 days of culture, the number of MCF-7 cells in each well was assessed from the reduction of the dye MTT (3-(4,5-dimethylthiazol-2-yl)-2,5-diphenyltetrazolium bromide), as described by F. Denizot and R. Lang, *J. Immunological Methods*, Vol. 89: 271–277 (1986). MTT was added to each well to a final concentration of 1 mg/ml and the cells were incubated for a period of three hours, after which reduced MTT was extracted using 95% ethanol and the optical density was measured at a wavelength of 570 nm.

For each vitamin $D_3$ analog, the $IC_{50}$ value was determined from a graph relating the optical density at 570 nm to the concentration used. The $IC_{50}$ value was defined as the concentration of the vitamin $D_3$ analog corresponding to half-maximal reduction in 570 nm absorbance.

| Vitamin $D_3$ Analogs | $IC_{50}$ nM |
|---|---|
| 1,25-Dihydroxy-cholecalciferol | 40 |
| 21-(3-Hydroxy-3-methyl)butyl-1,25-dihydroxy-cholecalciferol | 0.8 |

The results of the above test show that 21-(3-Hydroxy-3-methyl)butyl-1,25-dihydroxy-cholecalciferol is approximately 50 times more potent than 1,25-dihydroxy-cholecalciferol in inhibition of MCF-7 breast cells growth in culture.

EXAMPLE 14

Cell Proliferation Assay in ZR-75 Breast Cancer Cells

ZR-75 cells are human mammary carcinoma cells that are positive for estrogen receptors. The potential activity of vitamin $D_3$ analogs against breast cancer was assessed from inhibition of proliferation of ZR-75 cells in culture.

ZR-75 cells were plated at 12,500 cells/well in 24-well plates and incubated at 37° C. in 5% $CO_2$/95% air in RPMI medium containing 10% fetal bovine serum and 2 mM glutamine. Stock solutions of vitamin $D_3$ analogs were prepared at a concentration of 10 mM in absolute ethanol and stored at −20° C. under argon. One day after plating, ZR-75 cells were refed with either control medium or medium containing varying concentrations of the vitamin $D_3$ analog. After a further 10 days of culture, the number of ZR-75 cells in each well was assessed from the reduction of the dye MTT (3-(4,5-dimethyl-thiazol-2-yl)-2,5 diphenyltetrazolium bromide), as described by F. Denizot and R. Lang, *J. Immunological Methods*, Vol. 89: 271–277 (1986). MTT was added to each well to a final concentration of 1 mg/ml and the cells were incubated for a period of three hours, after which reduced MTT was extracted using 95% ethanol and the optical density was measured at a wavelength of 570 nm.

For each vitamin $D_3$ analog, the $IC_{50}$ value was determined from a graph relating the opitical density of 570 nm to the concentration used. The $IC_{50}$ value was defined as the concentration of the vitamin $D_3$ analog corresponding to half-maximal reduction in 570 nm absorbance.

| Vitamin $D_3$ Analogs | $IC_{50}$ nM |
|---|---|
| 1,25-Dihydroxy-cholecalciferol | 13 |
| 21-(3-Hydroxy-3-methyl)butyl-1,25-dihydroxy-cholecalciferol | 0.3 |

The results of the above test show that 21-(3-Hydroxy-3-methyl)butyl-1,25-dihydroxy-cholecalciferol is more than 40 times more potent than 1,25-dihydroxy-cholecalciferol in inhibition of ZR-75 breast cells growth in culture.

EXAMPLE 15

Oral Dosage Form Soft Gelatin Capsule

A capsule for oral administration is formulated under nitrogen in amber light from 0.01 to 25.0 mg of one of the compounds of the present invention in 150 mg of fractionated coconut oil, with 0.015 mg butylated hydroxytoluene (BET) and 0.015 mg butylated hydroxyanisole (BHA), filled in a soft gelatin capsule.

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not restrictive. The scope of the invention should, therefore, be determined with reference to the following appended claims, along with the full scope of equivalents to which such claims are entitled.

The patents, patent applications and publications cited in this application are hereby incorporated by reference in their entirety for all purposes to the same extent as if each individual patent, patent application or publication were so individually denoted.

What is claimed is:

1. A method of inducing inhibition of cell proliferation in a breast tumor comprising administering to a human in need thereof from about 0.01 to about 25 μgs of a compound of Formula I

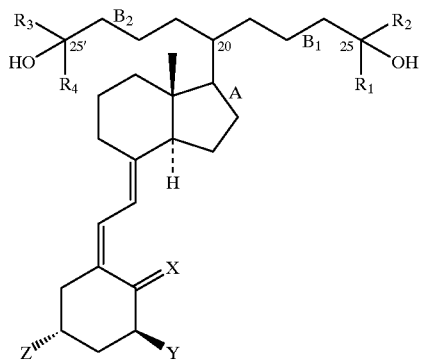
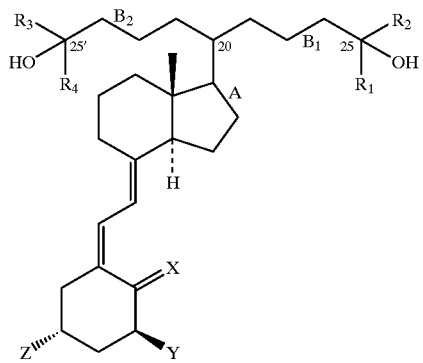

wherein:

X is $H_2$ or $CH_2$;

Y is hydrogen, hydroxy or fluorine;

Z is hydroxy;

$R_1$ and $R_2$ are a ($C_1$–$C_4$) alkyl or fluoroalkyl, or $R_1$ and $R_2$ together with $C_{25}$ form a ($C_3$–$C_6$) cycloalkyl or cyclofluoroalkyl;

$R_3$ and $R_4$ are a ($C_1$–$C_4$) alkyl or fluoroalkyl, or $R_3$ and $R_4$ together with $C_{25'}$ form a ($C_3$–$C_6$) cycloalkyl or cyclofluoroalkyl;

A is a single bond or a double bond;

$B_1$ is a single bond, an E-double bond, a Z-double bond or a triple bond; and $B_2$ is a single bond, an E-double bond, a Z-double bond or a triple bond.

2. The method of claim 1 wherein A is a single bond.
3. The method of claim 1 wherein Y is fluorine.
4. The method of claim 1 wherein Y is hydroxy.
5. The method of claim 1 wherein $B_1$ and $B_2$ are double bonds.
6. The method of claim 1 wherein $B_1$ and $B_2$ are triple bonds.
7. The method of claim 1 where $R_1$–$R_4$ are fluoroalkyl.
8. A method of treating inducing inhibition of cell proliferation in a breast tumor comprising administering to a human in need thereof from about 0.01 to about 25 μgs of a prodrug of a compound of Formula I wherein:

X is $H_2$ or $CH_2$;

Y is hydrogen, hydroxy or fluorine;

Z is hydroxy;

$R_1$ and $R_2$ are a ($C_1$–$C_4$) alkyl or fluoroalkyl, or $R_1$ and $R_2$ together with $C_{25}$ form a ($C_3$–$C_6$) cycloalkyl or cyclofluoroalkyl;

$R_3$ and $R_4$ are a ($C_1$–$C_4$) alkyl or fluoroalkyl, or $R_3$ and $R_4$ together with $C_{25'}$ form a ($C_3$–$C_6$) cycloalkyl or cyclofluoroalkyl;

A is a single bond or a double bond;

$B_1$ is an E-double bond, a Z-double bond or a triple bond; and $B_2$ is an E-double bond, a Z-double bond or a triple bond.

9. The method of claim 8 wherein A is a single bond.
10. The method of claim 8 wherein Y is fluorine.
11. The method of claim 8 wherein Y is hydroxy.
12. The method of claim 8 wherein $B_1$ and $B_2$ are double bonds.
13. The method of claim 8 wherein $B_1$ and $B_2$ are triple bonds.
14. The method of claim 8 where $R_1$–$R_4$ are fluoroalkyl.
15. The method of claim 1, wherein the compound of formula I is 21-(3-hydroxy-3-methyl)butyl-1,25-dihydroxycholecalciferol.

* * * * *